United States Patent [19]

Kronner

[11] Patent Number: 4,775,362

[45] Date of Patent: Oct. 4, 1988

[54] UTERINE MANIPULATOR WITH EXTERNALLY SECURABLE CLAMP

[76] Inventor: Richard F. Kronner, 1443 Upper Cleveland Rapids Rd., Roseburg, Oreg. 97470

[21] Appl. No.: 52,481

[22] Filed: May 21, 1987

[51] Int. Cl.⁴ .......................................... A61M 29/00
[52] U.S. Cl. ...................................... 604/96; 604/55
[58] Field of Search ........................... 604/96–103, 604/55; 128/656–658, 344; 24/486, 545, 557

[56] References Cited

U.S. PATENT DOCUMENTS

| | | | |
|---|---|---|---|
| 3,253,594 | 5/1966 | Matthews et al. | 604/96 |
| 3,453,700 | 7/1969 | Petertil et al. | 24/557 |
| 4,430,076 | 2/1984 | Harris | 128/658 |
| 4,723,556 | 2/1988 | Sussman | 604/97 |

Primary Examiner—John D. Yasko
Assistant Examiner—J. L. Kruter
Attorney, Agent, or Firm—Kolisch, Hartwell & Dickinson

[57] ABSTRACT

A uterine manipulator including a catheter tube with an insertable end adapted to be inserted into the uterus. An adjustable stop adapted to engage the cervix is mounted on and shiftable axially along the catheter tube. The stop is adjusted in position and secured in an adjusted position through operation of a digitally actuated clamp which is positioned outside the external opening of the vagina with the manipulator in place.

4 Claims, 1 Drawing Sheet

UTERINE MANIPULATOR WITH EXTERNALLY SECURABLE CLAMP

BACKGROUND AND SUMMARY OF THE INVENTION

Background and Summary of the Invention

This invention relates to uterine manipulators, and more particularly to a manipulator featuring an adjustable stop with is positionable against the cervix or outer end of the cervical canal by means accessible by the operator, i.e. located outwardly of the external opening of the vagina, with the manipulator inserted into the uterus.

A uterine manipulator is commonly used in properly positioning the uterus so that, for example, inaccessible areas may be viewed through a viewing scope passed through a small incision in the abdominal wall. A manipulator which includes an injector is usable in injecting fluids into the uterine cavity, a procedure followed, for instance, in determining fallopian tube patency by noting the flow of the injected fluid from the uterus and thence out of the fallopian tubes which are attached to the uterus.

One form of uterine manipulator which is known in the art is the one disclosed in U.S. Pat. No. 4,089,337. In the manipulator-injector disclosed in this patent, a disc or stop is provided which is biased by a spring to engage the cervix during manipulation of the uterus and which functions yieldably to hold an inflatable member against the junction of the uterine cavity with the inner end of the cervical canal. With this type of manipulator, it has been the practice to provide a preset collar or similar means which the spring reacts against when biasing the stop against the cervix.

Another form of manipulator is exemplified by the one disclosed in U.S. Pat. No. 4,430,076. In the manipulator of this patent, the stop which is positioned against the cervix or external opening of the cervical canal forms an integral part of an elongate handle which receives and firmly engages a catheter portion of the device.

In using manipulators of the above general description, and since the length of the cervical canal will vary from patient to patient, an operator will preset the adjustable components, i.e., the collar or the handle as the case may be, in an attempt thus to fit the manipulator for the particular patient involved The components are preset, since the construction of the manipulators is such that the components cannot be adjusted in position with the manipulators inserted inside the body. As an aid to making a proper setting, an operator typically might premeasure with a suitable measuring probe the combined distance of the length of the cervical canal and the length of the uterine cavity which joins with this canal. This procedure, however, produces only an approximation with respect to the optimum setting of the components, since the proportion of this measurement which makes up the length of the cervical canal will vary from patient to patient.

A general object of this invention is to provide an improved uterine manipulator featuring an adjustable stop for engaging the external opening of the cervical canal which may be adjusted by an operator externally of the vagina with the manipulator inserted into the uterus. The device permits accurate placement of the stop without the operator needing to determine the precise length of the cervical canal.

More specifically, the manipulator contemplated includes an adjustable clamp mechanism positioned remote from the insertable end of the manipulator and outside the external opening of the vagina with the manipulator inserted, and a compression and tension transmitting connector extending from the clamp mechanism to a stop provided for engagement with the external opening of the cervical canal.

In a specific and preferred embodiment of the manipulator, the clamp mechanism comprises opposed digitally operated members biased away from each other to produce a clamping position and movable toward each other under finger pressure for the purpose of releasing the clamp. The connector may take the form of a sheath encompassing a tubular portion of the manipulator which funnels or channels air to the inflatable member, the sheath having a nonclamping relationship with the tubular portion.

These and other objects and advantages are attained by the invention which will become more fully apparent from a reading of the following description to be taken in conjunction with the accompanying drawings.

Figure 1:
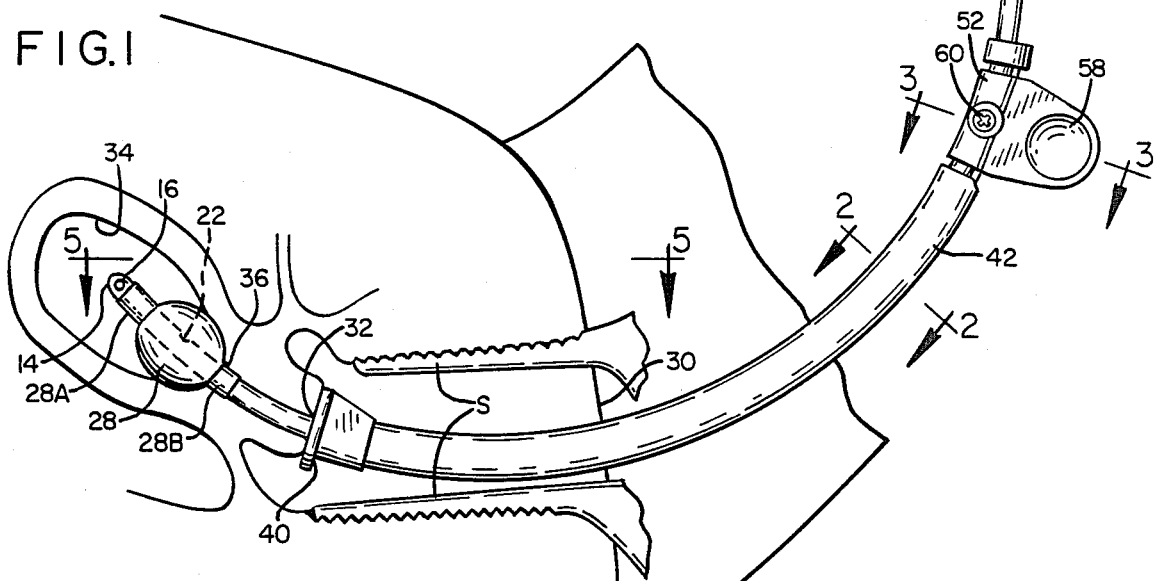
FIG. 1 is a view illustrating, in a simplified manner, the uterus of a patient, and a uterine manipulator as contemplated herein with an end thereof inserted into the uterus.
Figure 4:
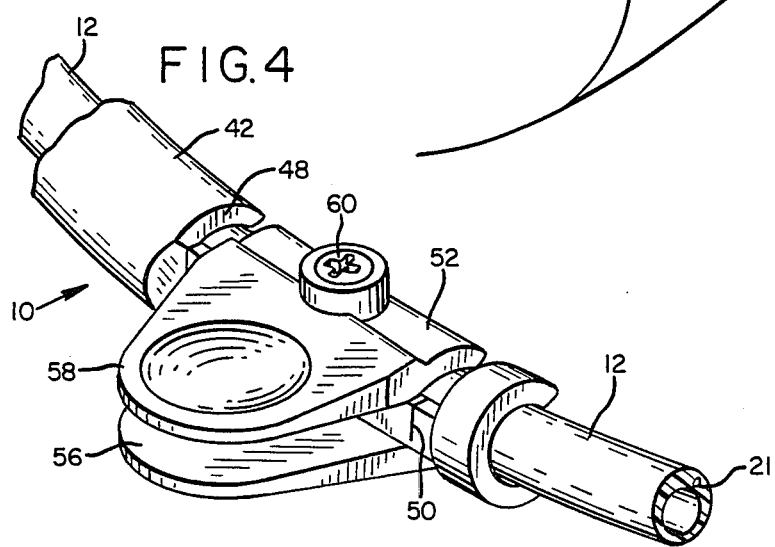
FIG. 4 is an enlarged view of a clamp mechanism in the device.
Figure 3:
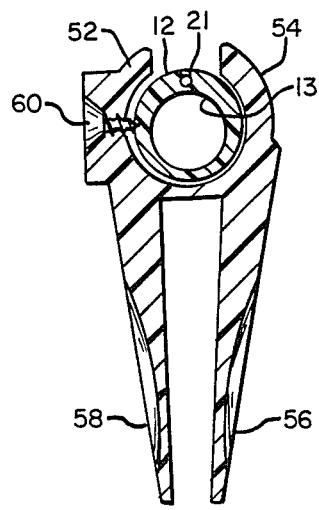
FIG. 3 is a cross-sectional view, also on a somewhat larger scale, taken generally along the line 3—3 in FIG. 1.

Referring now to the drawings, a uterine manipulator constructed according to the invention is shown generally at 10. Manipulator 10 includes an elongate catheter tube portion 12 which extends the length of the manipulator Such ordinarily may be made of a semi-rigid plastic material such as polyvinyl chloride. The insertable end of this tube, i.e. the end of the tube which is illustrated at the left in FIG. 1, is closed off with a rounded nose portion 14 provided with transversely extending ports 16 which connect with the interior of the tube. Joining with the opposite end (referred to herein as the exterior end) of the tube is a coupler 18 which enables the tube to be coupled with a syringe or other device actuatable to introduce fluid into the end of the tube. The internal wall 13 of the tube defines a passage extending the length of the tube for channeling fluid introduced into the tube through coupler 18 whereby such flows along the length of the tube to be expelled through ports 16.

Shown at 20 is an air line or tube which may be of a flexible plastic material and which enters catheter tube 12 adjacent the latter's exterior end and connects with a passage 21 extending along the length of the tube, passage 21 terminating at discharge port 22 formed in the side of tube 12 adjacent the insertable end of tube 12. Fluid, i.e. air, is introduced to air line or tube 20 through a coupler 24 forming the inlet end or port of the air line. The coupler is provided to enable the easy attachment of a syringe or other air injector to the inlet end of the air line. Interposed between the coupler and the air line is a pilot balloon 26, which on being expanded with air under pressure provides an indicator for indicating the degree of inflation that has occurred in an inflatable member, to be described.

Figure 5:
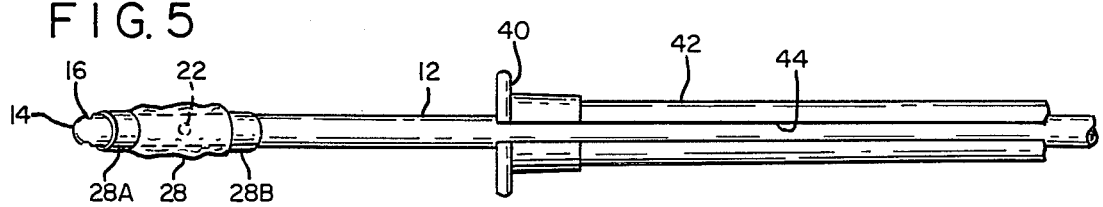
FIG. 5 is a view illustrating the insertable end portion of the manipulator as such would be viewed along the line 5—5 in FIG. 1.

Specifically, such inflatable member comprises a sleeve 28 of flexible resilient material mounted about the catheter tube 12 at the region of port 22 and with opposite end extremities 28A, 28B suitably secured to the catheter tube. The sleeve, in effect, forms a balloon which is extendable from the deflated state shown in FIG. 5 to the inflated state shown in FIG. 1 through the introduction of pressurized air to the interior of the sleeve.

In utilizing the manipulator of the invention, the insertable end of the manipulator is inserted through the external opening of the vagina indicated generally at 30 in FIG. 1 (with vaginal speculum S facilitating insertion), into the cervix or external opening of the cervical canal (shown at 32 in FIG. 1), through the cervical canal and into the uterine cavity of the uterus, shown at 34 in FIG. 1. The inflatable member or sleeve is inflated through the introduction of air and the manipulator retracted to bring the inflatable member into seated position against the region where the uterine cavity joins with the cervical canal, such being indicated at 36 in FIG. 1 and, for simplicity's sake, being referred to herein as the internal opening of the canal. To maintain such member in the seated position, a stop or abutment member movable along the catheter tube is brought up against the cervix, and the operator of the device does this through means accessible by the operator located outside the external opening of the vagina.

Figure 2:
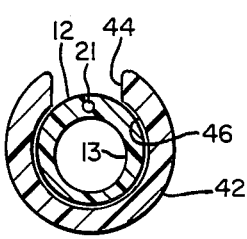
FIG. 2 is a cross-sectional view, on a somewhat larger scale, taken generally along the line 2—2 in FIG. 1.

Further explaining, indicated at 40 is a stop or abutment member taking the form of a disc-shaped enlargement integrally joined to the end of an elongate sheath element 42. The sheath element is slotted along its length with slot 44, with this slot extending through stop 40. As can be seen with reference to FIG. 2, the passage 46 which extends along the interior of the sheath element and which receives the catheter tube 12 has a diameter which is significantly greater than the outer diameter of the catheter tube. As a consequence, there is essentially no frictional engagement between the sheath and the catheter tube, i.e., a non-clamping relationship exists, the passage 46 serving as a guide slot for tube 12 when such is axially shifted therealong. The passage also provides sufficient confinement for tube 12 whereby the sheath may function as a stiffening handle when used to manipulate tube 12.

Sheath element 42, adjacent its end which is opposite the one having stop 40, referred to as the exterior end of the sheath element, is cut away as in region 48. The sheath element is made of a plastic, such as polyethylene, and the wall thickness of the sheath throughout most of the sheath is such as to impart a relatively stiff character through the sheath. In the cut away region, because of the reduced thickness that such results in, and because of the introduction of weakening slots such as the one shown at 50, a degree of flexible resilience is imparted to tab 52 relative to opposing side wall portion 54.

Integrally joined to side wall portion 54 and tab 52 are respective ones of a pair of opposed finger actuators 56, 58. These extend outwardly to one side of the sheath and are laterally spaced apart from each other. Tab 52, where such is opposite side wall portion 54, has a screw 60 mounted thereon with its inner end protruding beyond the inner surface of tab 52 and forming a detent projecting toward the side of tube 12. The projection of the screw inwardly toward the tube is selected to be such that, without digital pressure applied to the actuators, the resilience inherent in the tab and side wall portion 54 will cause the screw end to bite into the side of the tube effectively clamping the sheath whereby such is held from axial displacement relative to tube 12. With finger pressure applied to actuators 56, 58 outer extremities of the actuator move toward each other flexing the tab and side wall portion against the resilience of the sheath wall with the screw end moving clear of the side of tube 12. This releases the sheath for axial displacement relative to the tube. What has been described is a releasable clamp mechanism normally biased into clamping engagement with the side of the tube which is released digitally to accommodate displacement of the sheath along the tube.

In using the manipulator, the clamp mechanism is released and the sheath moved backwardly on the catheter tube so that the stop 40 is well inwardly from the insertable end of the manipulator and out of possible contact with the cervix with the manipulator initially positioned in place. The insertable end of the manipulator is inserted through the vagina and the cervical canal into the uterine cavity. After being so positioned, air under pressure is introduced through the air line or tube 20 to inflate the inflatable member with such positioned in the uterine cavity. The operator ther retracts the manipulator to the extent necessary to bring the now inflated inflatable member into snug adjacency with the internal opening 36 of the cervical canal.

To maintain this relationship, the operator then releases the clamp mechanism provided by the finger actuators rendering the sheath element easily slidable along the catheter tube. The sheath element is then displaced axially along the tube 12 to the extent necessary to bring stop 40 up against the external opening of the canal, i.e., cervix 32. With this relationship established, the clamp mechanism is released which serves to lock the sheath and its stop from axial displacement along the tube.

It will be noted that using the manipulator contemplated, no probing is necessary in an attempt to determine the combined length of the cervical canal and the uterine cavity. Furthermore, accurate placement of the stop results which is not possible even when such a probing measurement is taken, given the fact that with different patients that portion of the overall length of the uterus taken up by the cervical canal will vary.

While a particular embodiment of the invention has been described, it should be obvious that modifications and variations are possible without departing from the invention.

It is claimed and desired to secure by Letters Patent:

1. A uterine manipulator device comprising:
   an elongate tube having an insertable end adapted to be inserted through the cervical canal into the uterine cavity and an opposite end which locates outside the external opening of the vagina with the manipulator device in place, said tube having means defining a passage extending therealong and the passage having an inlet port adjacent its said opposite end and terminating in a discharge port adjacent said insertable end, said passage serving to channel fluid introduced thereinto along the tube with such delivered to sid discharge port, an inflatable member mounted on said discharge end of the tube with the interior thereof communicating with said discharge port and adapted to be inflated with said fluid channeled by said passage, an elongate plastic sheath having an internal passage extending therealong, said tube being lodged loosely within said passage with the sheath in non-clamping relation relative thereto and thus freely slidable relative to the tube, a stop integrally formed with one end of the sheath, also in loose slidable relation with respect to the tube, located adjacent but inwardly from the tube's insertable end, and a manually operable clamp joined to the opposite end of the sheath at a location which is exteriorly of the external opening of the vagina with the device in place and located adjacent but inwardly from the tube's opposite end having a clamping position wherein the clamp clamps onto the tube and a release position wherein the clamp releases the tube said sheath constituting a compression and tension transmitting connector extending between the clamp and stop and producing with release of the clamp and shifting of the clamp along the tube, corresponding movement in the stop enabling the stop to be properly positioned relative to the entrance of the cervical canal.

2. The uterine manipulator device of claim 1, wherein said clamp comprises opposed digitally operated members biased away from each to produce clamping of the tube and movable toward each other under digital pressure to release the clamp.

3. The uterine manipulator device of claim 2, wherein the tube is composed of a plastomer material and said clamp includes opposed portions that move against said tube to produce clamping of the tube, one of said portions including a projecting detent for engaging the tube.

4. The uterine manipulator of claim 1, wherein said clamp comprises a pair of opposed clamping portions of plastic and integrally formed with the plastic of the sheath and digitally operated members joining with said clamping portions extending laterally of the sheath and in opposed relation, the plastic of the sheath where joining with the clamp members having limited resilient flexibility and said resilient flexibility functioning to bias the clamp portions into engagement with the tube.

* * * * *